US005654312A

United States Patent [19]
Andrulis, Jr. et al.

[11] Patent Number: 5,654,312

[45] Date of Patent: Aug. 5, 1997

[54] TREATMENT OF INFLAMMATORY AND/OR AUTOIMMUNE DERMATOSES WITH THALIDOMIDE ALONE OR IN COMBINATION WITH OTHER AGENTS

[75] Inventors: Peter J. Andrulis, Jr., Bethesda; Murray W. Drulak, Gaithersburg, both of Md.

[73] Assignee: Andrulis Pharmaceuticals, Beltsville, Md.

[21] Appl. No.: 475,426

[22] Filed: Jun. 7, 1995

[51] Int. Cl.[6] ................................................. A61K 31/445
[52] U.S. Cl. .................. 514/279; 514/290; 514/291; 514/292; 514/323; 514/408; 514/410; 514/411; 514/422; 514/424; 514/425; 424/450

[58] Field of Search ....................... 514/279, 290, 514/291, 292, 323, 408, 410, 411, 422, 424, 425; 424/450

[56] References Cited

U.S. PATENT DOCUMENTS

| 5,434,170 | 7/1995 | Andrulis, Jr. ........................... 514/323 |
| 5,443,824 | 8/1995 | Piacguadio .......................... 424/78.02 |

*Primary Examiner*—Nathan M. Nutter
*Attorney, Agent, or Firm*—Isaac Angres

[57] ABSTRACT

Methods of treatment for inflammatory and autoimmune dermatoses which comprises topical and/or systemic administration of a therapeutically-effective amount of thalidomide alone or in combination with other dermatological agents.

19 Claims, No Drawings

TREATMENT OF INFLAMMATORY AND/OR AUTOIMMUNE DERMATOSES WITH THALIDOMIDE ALONE OR IN COMBINATION WITH OTHER AGENTS

FIELD OF THE INVENTION

The present invention relates to novel methods for treating inflammatory and/or autoimmune dermatoses with thalidomide alone or in combination with other agents. The present invention also relates to methods of treating dermatoses with inhibitors of cytokine and/or growth factors such as those agents inhibitory to basic fibroblast growth factor (bFGF), Tumor Necrosis Factor (TNF-alpha), and Interleukin-1 beta (IL-1 beta) as well as pharmaceutical compositions containing relevant cytokine/growth factor inhibitors and/or other drug used to treat dermatoses.

BACKGROUND OF THE INVENTION

Inflammatory dermatoses describe a group of diseases involving the layers of skin below the epidermis that have an inflammatory component. Inflammation may be triggered by a number of external events ranging from exposure to UV light from the sun to an allergen. Thalidomide has been demonstrated to have an inhibitory effect on the pro-inflammatory cytokines. It has been shown to inhibit TNF-alpha production in erythema nodosum leprosum patients (Sarno et al., *Clin. Exp. Immunol*, 84:103–8, 1991) and in vitro stimulated monocytes (Sampaio et al., *J. Exp. Med.*, 173:699–703, 1991). Moreira et al. (*J. Exp. Med.*, 177:1675–80, 1993) reported that thalidomide acts by enhancing TNF-alpha m-RNA degradation. Shannon et al. (*Amer. Society for Microbiology Ann. Mtg.*, Abs. U-53, 1990) indicated thalidomide inhibited IL-1 beta production in vitro. Such an inhibitory effect on IL-1 beta may be direct or indirect through TNF-alpha as suggested by Moreira et al. (1993).

IL-1 beta and TNF-alpha are important factors in induction of endothelial cell-leukocyte receptors during inflammation, such as E-selectin (Bevilacqua et al., *Science*, 243:1160–65, 1989) VCAM 1 (Elices et al., *Cell*, 60:577–84, 1990) and ICAM (Rothlein et al., *J. Immunol*, 137:1270–4, 1986), in vitro and in the dermal vasculature in vivo. Expression of cellular receptors on the surface of endothelial cells facilitates the binding of inflammatory cells that is a precondition to transendothelial migration occurring during inflammation. Thalidomide also has an anti-angiogenic effect since TNF-alpha stimulates endothelial cell motility in vitro (Leibovich, *Nature*, 329:630–32, 1987; Rosen et al., In: Cell Mtility Factors Goldberg, I, and Rosen E. M., Editors, Birkhauser-Verlag, *Basel*, pg. 194–205, 1991) and has strong angiogenic activity in vivo (Leibovich et al., 1987; Frater-Schroder et al., *Proc. Natl. Acad. Sci. (USA)*, 84:5277–5291, 1987). D'Amato et al. (*Proc. Natl. Acad. Sci. (USA)*, 91:4082–5,1994) showed that thalidomide was an effective inhibitor of angiogenesis induced by bFGF.

In 1965 Sheskin (*Lepr. Rev.*, 36:183–7) administered thalidomide to leprosy patients suffering from the complication erythema nodosum leprosum (ENL), to sedate them. ENL is characterized by recurrent erythematosus nodules on the skin, weight loss, mania, neuritis, fever, malaise, and sometimes epididyo-orchitis. Within 12 hours of thalidomide administration nodular eruptions began to heal and within two days fever declined and the ENL lesions had completely resolved. In 1971 Iyer et al., *Bull. WHO*, 45:719–32, presented the results of a double blind clinical trial conducted in four countries and coordinated by the World Health Organization, which tested the efficacy of thalidomide versus aspirin for treatment of ENL. The conclusions reached supported Sheskin's original observations about the effectiveness of thalidomide for treatment of ENL. Wemambu et al. (*Lancet*, 2:933–5, 1969) observed necrotizing vasculitis of veins and arteries in patients with ENL. This was accompanied by initial neutrophil accumulation at disease sites as well as deposits of complement and immunoglobulin. This description of the disease process in ENL is consistent with that of an Arthus Reaction. However, others in the field disputed this explanation for ENL pathogenesis. Goihman-Yahr et al., *Int. Arch. Allergy Appl. Immun.*, 57:317–332 (1978) showed in a study of neutrophil activation in ENL patients just before and during treatment with thalidomide that tissue damage was not due solely to neutrophil activation as occurs in immune complex diseases, but rather neutrophils appeared to be activated by an undefined lymphokine. This group went on to state that the therapeutic effect of thalidomide was not due to inhibition of neutrophil activation. Sarno et al. (*Clin. Exp. Immunol.*, 84:103–8, 1991) showed that TNF-alpha levels were elevated in ENL patients and that TNF-alpha had a major role in the pathogenesis of this disease. Thalidomide was shown to inhibit TNF-alpha production in these ENL patients. Sampaio et al. (*J. Inf. Dis.*, 168:408–14, 1993) confirmed Sarno's results as to the inhibitory effect of thalidbmide on serum TNF-alpha levels, but also demonstrated a reduction of dermal infiltration of polymorphonuclear leukocytes and T cells.

The fortuitous finding that thalidomide was effective in treating ENL stimulated other investigators to look at the efficacy of thalidomide for treating other dermatoses with a possible inflammatory and/or autoimmune pathogenesis.

Actinic prurigo is an inherited dermatological condition which afflicts 1–2% of the America Indian population. It often develops before puberty and presents initially as persistent eczematous eruptions on the face and other sun exposed areas. Later it spreads to sun protected areas of the body. Its etiology is unknown. Londono (*Int. J. Dermatol.*, 12:326–8, 1973) was the first to report using thalidomide as a treatment for actinic prurigo. He administered 300 mg of thalidomide per day to 34 patients until clinical improvement was noted and then reduced the dosage progressively. There was notable improvement in 32 of the 34 patients, however, it took up to several months for clinical improvement to occur as compared to the short period of time it took for complete resolution of ENL lesions. Londono postulated it had an immunological etiology. Lovell et al. (*Brit. J. Dermatol*, 108:467–71, 1983) treated 14 actinic prurigo patients with 50–100 mg of thalidomide per day for children and 100–200 mg of thalidomide per day for adults, for variable periods of time. Eleven patients had long term clinical improvement and three were free of symptoms even after thalidomide was discontinued. No side effects were noted.

Prurigo nodularis is a dermatological condition characterized by excoriated and hyperpigmented dome shaped nodules. Lesions are extremely pruritic and maybe triggered by exposure to sunlight or insect bites or may be idiopathic in nature. Results of skin biopsies for this condition are indicative of chronic dermatitis or lichen simplex chronicums. Diagnosis is made on the basis of clinical criteria. Mattos (*Bol. Div. Nac. Lepra.*, 32:71) in 1973 was the first investigator to use thalidomide to treat prurigo nodularis. One of the two patients treated received 200 mg per day of thalidomide and the other patient, a woman, received 300 mg daily. Both patients had excellent clinical responses to the therapy after several weeks. Sheskin (*Hautarzt*, 26:215, 1975) reported treating three prurigo nodularis patients with thalidomide. These patients suffered from the disease for eight to twenty-four years, but responded clinically within a few weeks of initiation of thalidomide therapy. Other studies (Van den Broek, *Arch. Dermatol*, 116:571, 1980; Nikolowski, *Hautarzt*, 31:565, 1980; Winkelmann et al., *Acta. Dermato-Venereologica*, 64:412–7, 1984) have confirmed this clinical improvement in patients, with the intensive itch that accompanies this condition subsiding within 2–3 weeks of the start of 200 mg per day of thalidomide. However, in these studies it was noted that it takes at least six months of thalidomide therapy before strongly lichenified lesions completely heal.

Discoid lupus erythematosus is a chronic recurrent skin infection predominantly afflicting women. Skin lesions consist of red macules that are covered with scales and extend into follicles. Lesions are characteristically distributed in a butterfly pattern across the cheeks and bridge of the nose, but may occur in other body areas as well. The disease is believed to have an autoimmune etiology. The disease may be induced by administration of certain drugs. Barba-Rubio and Gonzalez, *Derm. Rev. Mex.*, 19:131 (1975) treated 20 discoid lupus erythematosus patients with 300 mg of thalidomide per day. Within two weeks 19 of these patients responded clinically and the medication was then reduced to a maintenance dose of 25 mg per day. Other groups (Knop et al., *Arch. Dermatol. Res.*, 271:165–70, 1983; Levi et al., *Giorn. Ital. Derre. Vener*, 115:471, 1980; Samsoen et al., *Ann. Dermatol Venereol (Paris)*, 107:515–23, 1980) confirmed the effectiveness of thalidomide therapy in treating discoid lupus erythematosus patients refractory to other treatments such as steroids. In most instances a clinical effect was detected within 14 days of initiation of 100–200 mg per day of thalidomide, however, a total and definite recovery was seen in only 15–20% of patients. In most patients a 25–50 mg per day maintenance dose of thalidomide was required to sustain a clinical improvement.

Thalidomide has also been used successfully to treat Behcet's syndrome, a rare and severe illness of unknown etiology often afflicting young males. It is characterized by progressive ulceration of the mouth and genitalia, uveitis, and retinal vasculitis. There also may be atrophy of the gastrointestinal tract and pulmonary or myocardial fibrosis. Thalidomide therapy was an important breakthrough, because prior to this there was no specific treatment for Behcet's syndrome. Steroids proved to be only of limited usefulness in treating Behcet's and only symptomatic or supportive measures were being prescribed (Mamo et al., *Arch. Ophthamol*, 71:4–14, 1964). Saylan and Saltik (*Arch. Dermatol*, 118:536, 1982) were the first to use thalidomide to treat 22 patients with Behcet's syndrome who had deep and persistent oral aphthae. Patients were initially administered 400 mg per day of thalidomide for five days followed by 200 mg per day for 15 to 60 days. This regimen resulted in rapid and complete healing of aphthae. Torras et al. (*Arch. Dermatol*, 118:875, 1982) found that there was complete healing of giant aphthae in eight of nine Behcet's patients treated with 100 mg per day of thalidomide for 10 days. Jorizzo et al. (*Arch. Int. Med.*, 146:878–81, 1986) reported similar success with thalidomide in five patients with Behcet's syndrome. In 1993 Denman et al., *Rev. Med. Int.*, 14:(suppl 1) 495, treated 39 patients with Behcet's syndrome with 50 mg of thalidomide three nights per week for a mean time of 35.9 months and a maximum treatment time of up to 65 months. Concomitant treatment in this patient group included 10 patients on prednisone, 3 on azathioprine and 1 patient on cyclosporin. Mucosal lesions healed in all patients. Moulin et al. (*Ann. Dermatol Venereol*, 110:611, 1983) used 100 mg per day of thalidomide to treat six patients with a Jessner-Kanof lymphocytic infiltration of the skin. This disease is characterized by numerous lesions on the face and back with lymphocytic infiltration of the dermis, but little modification of the epidermis. In five of the six patients there was clinical improvement in skin lesions, however, most patients relapsed if treatment was stopped. A 25–50 mg per day maintenance regimen helped three of the five patients to maintain normal skin over two years. Eravelly and Waters, *Lancet*, i:251 (1977) treated a patient with a relapsing non-suppurative panniculitis termed Weber Christian Disease, with 300 mg per day of thalidomide for three weeks which was reduced to 200 mg per day and then to 100 mg per day after 10 days. Therapy was stopped after 13 weeks. The patient's skin lesions steadily regressed during therapy and it was reported that a disease free state was maintained for 13 months after thalidomide was stopped. Thalidomide has also been used to treat recurrent erythema multiforme, a flu like syndrome in which blisters appear on mucous membranes of the mouth followed by lesions on the hands and feet. Corticosteroids are used to treat severe forms of the condition, however, the side effects of this therapy detract significantly from its advantages. Bahmer et al., *Acta. Derm. Venereal*, 62:449 (1982) treated a patient who had recurrent erythema multiforme with 200 mg of thalidomide per day. Within a few days the mucosal membrane and skin lesions healed and the daily dosage of thalidomide was lowered. The patient has been maintained in a disease free state by administration of 100 mg of thalidomide per day.

As indicated oral administration of thalidomide has been successfully used to treat a limited number of dermatoses that may have an autoimmune and/or inflammatory component associated with them. Topical application of thalidomide is a useful therapeutic approach for disease states with an autoimmune and/or inflammatory basis. Furthermore, thalidomide may be used alone to treat dermatoses with an autoimmune and/or inflammatory basis or in unique combinations with other cytokine/growth factor inhibitors and/or other anti-inflammatory and/or anti auto-immune agents and/or other physical and/or chemical dermatological treatments. An example of such combination therapy could involve thalidomide given with pentoxifylline and a glucocorticoid such as dexamethasone. The activity of each of these agents would be expected to enhance that of the other two in inhibiting TNF-alpha synthesis since each of these agents acts as an inhibitor at a different point in this synthesis. Pentoxifylline inhibits TNF-alpha gene transcription (Doherty et al., *Surgery (St. Louis)*, 110:192, 1991), while thalidomide enhances TNF-alpha m-RNA degradation (Moreira et al., 1993) and glucocorticoids such as dexamethasone inhibit TNF-alpha m-RNA translation (Han et al., *J. Exp. Med.*, 172:391, 1990).

Thalidomide has been administered orally, however, it may be used topically to treat dermatoses with an autoimmune and/or inflammatory component associated with them, such as, for example, using creams, ointments or lotions or in combination with other therapies.

Thalidomide was first synthesized and marketed in the 1950's as a sedative. The toxicity of the compound was so low that a dose killing 50% of animals ($LD_{50}$) could not be established. Thalidomide was therefore thought to be a safer alternative to barbiturates. In 1961 thalidomide administered to pregnant women resulted in an epidemic of congenital malformation. The incidence of malformed babies paralleled the sales of thalidomide and quickly dropped off when thalidomide was removed from the market.

Oral administration of thalidomide in the range of 100–200 mg in adult humans results in a peak blood level of 0.9–1.5 mg/liter after 4–6 hours. Hydrolytic cleavage of thalidomide occurs in vitro, the rate of which increases as the pH increases. However, hydrolytic cleavage of thalidomide in serum is much slower than in vitro at pH 7.4. This may be due to thalidomide being highly bound to plasma proteins. Studies in animals demonstrated high thalidomide concentrations in the gastrointestinal tract, liver and kidneys with lower concentrations in muscle, brain and adipose tissue. In pregnant animals, thalidomide can pass across the placenta.

Although a complete study of thalidomide metabolism in humans has not been performed, in animals the main pathway for thalidomide breakdown appears to be nonenzymatic hydrolytic cleavage. Even though immunomodulatory effects of thalidomide have not been clearly defined at the molecular level, thalidomide has been used to treat the following immunologically-based diseases: acute aphthous ulcers (Jenkins et al., *Lancet*, 2:1424–6, 1984; Grinspan, *J. Amer. Acad. Dermatol*, 12:85–90, 1985; Revuz et al., *Arch. Dermatol*, 126:923–7, 1990), graft vs host disease (Lim et al., *Lancet*, 1:117, 1988; McCarthy et al., *Lancet*, 2:1135, 1988; Henley et al., *Lancet*, 2:1317, 1988), erythema nodosum leprosum (Sheskin, *Lepr. Rev.*, 36:183–7, 1965; Sheskin and Convit, *Int. J. Lerp.*, 37:135–46, 1969; Pearson and Vedagirl, *Lepr. Rev.*, 40:111–16, 1969), Behcet's syndrome (Saylan and Saltik, 1982; Jorizzo et al., *Arch. Int. Med.*, 146:878–81, 1986), actinic prurigo (Londono, *Int. J. Dermatol*, 12:326–8, 1973; Lowell et al., 1983), ulcerative colitis (Waters et al., *Brit. Med. J.*, 1:792, 1979) and discold lupus erythematosus (Knop et al., *Arch. Dermatol Res.*, 271:165–70, 1981). In these studies, dosages of thalidomide ranging from 100 mg/day to 800 mg/day were administered without serious side effects.

SUMMARY OF THE INVENTION

The primary objective of the present invention is to provide a method for the treatment of dermatoses with an autoimmune and/or inflammatory component with inhibitors of cytokine and/or growth factors.

A further objective of the present invention is the treatment of dermatoses with an autoimmune and/or inflammatory component with thalidomide alone or in combination with other agents that inhibit cytokines and/or growth factors, and/or with other classes of therapeutics used to treat dermatoses.

Another objective of the present invention is the use of thalidomide alone or in combination with other agents.

Another objective of the current invention is to provide a method for treating dermatoses with an autoimmune and/or inflammatory component with thalidomide at a given regimen.

An additional objective of the current invention is to provide compositions of matter comprising inhibitors of cytokine growth factors with agents of other classes of therapeutics used to treat dermatoses.

A further objective of the present invention is a method for the treatment of dermatoses which comprises therapy with thalidomide and other drugs on alternative days by diverse schedules.

An additional objective of the current invention is to utilize thalidomide alone or in combination with other inhibitors of cytokines and/or growth factors and/or other treatments for dermatoses as a maintenance therapy to prevent the relapse of dermatoses.

A still further objective of this invention is to use thalidomide alone or in combination with other inhibitors of cytokines and/or growth factors and/or other treatments for dermatoses as a prophylactic therapy for individuals believed to be susceptible to developing a certain type of dermatoses.

DESCRIPTION OF THE PREFERRED EMBODIMENTS

The present invention is directed to a method for the topical and/or systemic treatment of inflammatory and autoimmune dermatoses in a mammal which comprises applying and/or administering to said mammal a composition comprising: (a) an effective amount of thalidomide and (b) a therapeutically-acceptable vehicle for the thalidomide.

The instant invention is also directed to a method for the topical and/or systemic treatment of inflammatory and autoimmune dermatoses in a mammal which comprises applying to involved areas of the body of and/or administering to said mammal a composition comprising: (a) an inhibitor selected from the group consisting of cytokine inhibitors, growth factor inhibitors and mixtures thereof and (b) a therapeutically acceptable vehicle. The preferred cytokine and growth factor inhibitors are selected from the group consisting of TNF-alpha inhibitors, basic fibroblast growth factor inhibitors and IL-1 beta inhibitors. Typical inhibitors include thalidomide and pentoxifylline but the invention is not limited to those.

The following is a list of examples of dermatological conditions for which thalidomide therapy as proposed in this application is useful. However, proposed thalidomide treatments will not be limited to these indications since there may be other dermatological conditions not mentioned here where thalidomide may also be effective as a therapeutic:

(a) Dermatologic Allergies: such as contact dermatitis, photoallergic dermatitis; industrial dermatoses caused by exposure to a variety of compounds used by industry that are contact irritants; atopic eczema (infantile and adult), dermatoses caused by drugs and nummular eczema.

(b) Autoimmune Skin Diseases: such as acute, chronic and physical urticarias, for example solar, cholinergic, pressure and cold urticarias. Atopic dermatitis; Mast Cell Disease, Bullous Pemphigoid; Pemphigus Vulgaris; necrotizing vasculitis; lupus erythematosus (discold and systemic); dermatitis herpetiformis.

(c) Pruritic Dermatoses: such as winter, senile and essential pruritus, pruritus ani, eternal otitis and genital pruritus.

(d) Vascular Dermatoses: such as erythema multiforme, erythema nodosum, stasis dermatitis, purpuric dermatoses such as thrombocytopenic purpura and Henochs purpura, ecchymoses, stasis purpura, primary and secondary telangiectases.

(e) Seborrheic Dermatitis: such as Acne and Rosacea (f) Papulosquamous Dermatoses: such as Psoriasis, Pityriasis rosea, tinea versicolor, lichen planus.

(g) Bacterial Dermatoses: Pyoderma such as impetigo, ecthyma, folliculitis, furunles styes, carbuncles, sweat gland infections, erysipelas, erythrasma, infected ulcers, infected eczematoid dermatitis.

(h) Systemic Bacterial Infections With Skin Manifestations: such as scarlet fever, granuloma inguinale, chancroid, tuberculosis, leprosy, gonorrhea, rickettsial diseases, actinomycosis, syphilis.

(i) Vital Skin Infections: such as those caused by Herpes simplex virus, Kaposi's varicelliform eruption, zoster, chickenpox, smallpox, vaccinia, cowpox, warts, molluscum contagiosum, lymphogranuloma venereum, exanthematous diseases such as German measles, roseola and erythema infectiosum.

(j) Mycolic Skin Infections: such as Tinea (superficial fungal infections of the skin in various body sites), Sporotrichosis, North American Blastomycosis.

(k) Granulomatous Dermatoses: Such as Sarcoidosis, granuloma annulare, silica induced granulomas.

(l) Parasitic Skin Infections: such as Scabies, Pediculosis (m) Bullous Dermatoses (n) Exfoliative Dermatitis: primary and secondary (o) Pigmented Dermatoses: such as Chloasma (Melasma) and Vitiligo.

(p) Collagen Diseases: such as lupus erythematosus, scleroderma, dermatomyositis.

(q) Dermatoses Due To Internal Diseases: such as Kaposi's sarcoma, pyoderma gangrenosum associated with ulcerative colitis, ulcers due to diabetes, xanthomas.

(r) Diseases of Mucous Membranes: such as aphthous ulcers.

(s) Dermatoses Due To Physical Agents: such as sunburns and radiodermatitis.

(t) Photosensitive Dermatoses: Exogenous-type:such as drug-induced photodermatitis, contact dermatitis with photoallergic components.

Endogenous-type: such as porphyrias, collagen vascular disorders such as lupus erythematosus, dermatomyositis and polymorphous light eruptions.

There are three main principles that should be adhered to when treating dermatoses:

(1) the type of skin lesion is more important than its cause. For example wet lesions should be treated with wet dressings, dry lesions with a salve.

(2) never overtreat a skin lesion, since overuse of chemicals to treat a lesion can lead to contact dermatitis.

(3) the patient must be adequately instructed with reference to applying prescribed medication.

There are two general forms of treatment for dermatoses: (1) physical therapies (2) chemical therapies including topical and systemic administration of agents.

Physical therapies include but are not exclusive to:

Hydrotherapy: Such as medicated or non-medicated wet compresses and baths.

Electrosurgery: Such as electrodesiccation or fulguration, electrocoagulation, electrosection, electrocautery and electrolysis.

Cryosurgery: Such as those procedures employing solid carbon dioxide, liquid nitrogen or from freon 114.

Radiation: Such as ultraviolet therapy using hot quartz mercury vapor amps, fluorescent sunlamps, UVA lamps and cold quartz lamps; x-ray therapy and lasers.

Chemical therapy includes but is not exclusive to:

Topical Medications (a) Anti pruritic agents, which relieve itching, such as 0.25% menthol, 0.5% phenol, 2% camphor and 2–10% coal tar solutions.

(b) Keratoplastic agents, which increase the thickness of the horny layer of the skin, such as 1–2% salicylic acid.

(c) Emollients, which often soften surface layers of skin, such as petrolatum, Nivea oil and mineral oil.

(d) Antiseptics, which inhibit and/or destroy fungi and/or bacteria, such as 3% Vioform, 3–10% ammoniated mercury, antifungal agents such as Whitfields ointment, antibiotics such as 3% terramycin, 0.5% neomycin, 0.1% garamycin and 3% aureomycin.

(e) Antieczematous Agents, which remove oozing and vesicular excretions, such as Burows solution, soaks or packs, 2–5% coal tar solutions and 0.5–2% hydrocortisone.

(f) Keratolytic agents, which remove or soften the horny layer of the skin, such as 4–10% salicylic acid, 2–4% resorcinol and 4–10% sulfur.

(g) Antiparasitics, which inhibit or destroy infestations by parasites, such as Kewell cream for scabies and pediculosis and Eurax lotion for scabies.

Topical medications are delivered to the effected site including but not exclusive to the following methods:

(a) Baths: such as tar baths, starch baths, colloidal oatmeal baths, oil baths.

(b) Soaps and Shampoos: such as Oilatum and Dial soap, Selsun Shampoo and tar shampoos.

(c) Wet Dressings or Soaks: such as Burows or vinegar solutions.

(d) Powders: such as purified Talc, Tinactin and Mycostatin.

(e) Pastes: such as zinc oxide.

(f) Tinctures and Aqueous Solutions: such as thimerosal tincture, methiolate tincture, betadine.

(g) Shake lotions: such as Calamine, alcoholic and nonalcoholic shake lotions.

(h) Aerosols and Foams: such as corticosteroids, antibiotics and antipuritics.

(i) Medicated Tape: Such as Cordran.

(j) Transdermal Drug Delivery: such as Menorest which utilizes matrix technology in which the adhesive acts as a drug platform and a means whereby the delivery system can be attached to the skin.

(k) Creams and Ointments: such as those with water washable cream bases, those with ointment bases, antifungal antibiotics, corticosteroids, antipruitic creams and fluorinated corticosteroids.

(l) Oils and Emulsions: such as zinc oil, bath oils, hand and body emulsions.

II. Systemic Medications

Although many dermatoses can be adequately treated with physical therapies or topical medications in certain instances systemic chemotherapy is superior. The following list of chemotherapeutic agents used systemically to treat dermatoses is not a comprehensive one but rather consists of examples of commonly used groups of drugs.

(a) Corticosteroids:

This group of agents is used to treat inflammation of the skin having many different etiologies. Examples of indications in which systemically administered corticosteroids are employed as therapeutics include psoriasis, erythema nodosum leprosum, discold lupus erythematosus, urticaria, different types of pruritis, pemphigus and keloids. Systemic administration of corticosteroids, however, is less than ideal therapy with the potential for any of the following side effects developing especially upon prolonged usage: hyperglycemia, deposition of fat, sodium retention, potassium loss, edema, thrombosis, osteoporosis, hypertension and cardiac failure.

(b) Antihistamines:

This group of agents has an antipruritic effect. It includes alkylamines, phenothiazines, ethylenediamine, ethanolamine, and piperazine.

(c) Retinoids:

These compounds are synthetic and natural forms of vitamin A. These include isotretinoin and etretinate. Retinoids are used to treat acne vulgaris or rosacea and psoriasis. Side effects include conjunctivitis, cheilitis, pruritis, myalgia, arthralgia, alopecia, lethargy and dryness of mucous membranes. These compounds are also teratogens.

(d) Anti-cancer Agents:

This group includes alkylating agents and anti metabolites and is used on a limited basis to treat certain skin conditions.

(e) Anti Microbial Compounds:

This group includes antibiotics, antibacterial, antifungal, antiviral and antiparasitic agents. A novel use for one group of antiparasitic agents, the antimalarials, is to treat discold lupus erythematosus.

In treating Kaposi's Sarcoma, an ointment containing 10% by weight of thalidomide is applied to the lesion. In an alternative embodiment, Kaposi's Sarcoma is treated concurrently by topical and oral treatment. For example, a patient presenting with Kaposi's Sarcoma is treated daily for two to four weeks with a dosage amount of 50 mg of thalidomide a day while an ointment containing 10% by weight thalidomide is applied to the lesion three times a day for two to four weeks.

When used alone, the topically effective amounts of thalidomide are typically 5 to 15% by weight in an ointment and is applied one to three times a day for a period of time to induce regression of the dermatoses.

Under certain circumstances, it is desirable to administer thalidomide therapy simultaneously with other dermatological active agents. For example, a cream containing 5% by weight of thalidomide can be administered three times a day while the patient is being given a topical treatment with 1% hydrocortisone. Concurrent administration of oral thalidomide with topical thalidomide is also a desirable therapeutic goal.

Additionally, applicants propose to use thalidomide alone or in combination with other inhibitors of cytokines and/or growth factors to treat dermatoses. An example of such a combination therapy utilizes thalidomide given with pentoxifylline and a glucocorticoid such as dexamethasone. The activity of each of these agents would be expected to enhance that of the other two in inhibiting TNF alpha synthesis since each of these agents acts as an inhibitor at a different point in this synthesis. Pentoxifylline inhibits TNF alpha gene transcription, while thalidomide enhances TNF alpha m-RNA degradation and glucocorticoids, such as dexamethasone, inhibit TNF alpha m-RNA translation.

The precise amount of thalidomide used alone or with other dermatologic agents varies depending, for example, on the condition for which the drug is administered and the size and kind of the mammal. Generally speaking the thalidomide can be employed in any amount effective in the treatment of dermatoses.

For humans, typically-effective amounts of thalidomide for use in the topical dosage forms compositions of the present invention range from 5–15% by weight active, however, greater amounts may be employed if necessary. This range is based on administration to a 70 kg human. Of course the amounts of each compound selected will depend on the severity of disease state. One skilled in the art can adjust the dosage forms to achieve the desired therapeutic levels.

The compound of the present invention can be prepared and administered in a wide variety of oral dosages ranging in amounts from 50 mg/day to 250 mg/day and dosages administered by other routes. It will be obvious to those skilled in the art that the following dosage forms may comprise as the active component either thalidomide alone or in combination with other compounds. Preferably the compounds of the present invention are administered orally, intramuscularly, topically, subcutaneously, or intravenously. Topical administration is particularly preferred.

For preparing pharmaceutical compositions from the compounds of the present invention, pharmaceutically-acceptable carriers can be either solid or liquid. Solid form preparation include powders, lotions, creams, ointments, tablets, pills, capsules, cachets, suppositories, and dispensable granules. A solid carrier can be one or more substances which may also act as diluents, flavoring agents solubilizers, lubricants, suspending agents, binders, preservative, tablet disintegrating agents, or an encapsulating material.

In powders, the carrier is a finely divided solid which is in a mixture with the finely divided active component.

In tablets, the active component is mixed with the carrier having the necessary binding properties in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methycellulose, sodium carboxymethylcellulose, a low melting wax, cocoa butter, and the like. The term "preparation" is intended to include the formulation of the active compound with encapsulating material as a carrier providing a capsule in which the active component, with or without other carriers, is surrounded by a carrier, which is thus in association with it. Similarly, cachets and lozenges are included. Tablets, powders, capsules, pills cachets, and lozenges can be used as solid dosage forms suitable for oral administration.

For preparing suppositories, low melting wax, such as mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations such as lotions or creams include solutions, suspensions, and emulsions, for example, water or DMSO/propylene glycol solutions. For parenteral injection, liquid preparations can be formulated in solution in DMSO polyethylene glycol solution or DMSO-water solutions.

Liquid suspensions suitable for oral use can be made by dispersing the finely divided active component in an appropriate liquid with viscous material, such as natural or synthetic gums, resins, methycellulose, sodium carboxymethylcellulose, and other well-known suspending agents.

Also included are solid form preparations which are intended to be converted, shortly before use, to liquid form preparations for topical or systemic administration. Such liquid forms include solutions, suspensions, and emulsions. These preparations may contain, addition to the active component, colorants, flavors, stabilizers, buffers, artificial and natural sweeteners, dispersants, thickeners, solubilizing agents, and the like.

The pharmaceutical preparation is preferably in unit dosage form. In such form, the preparation is subdivided into unit doses containing appropriate quantities of the active component. The unit dosage form can be a packaged preparation, the package containing discrete quantities of preparation, such as packeted tablets, capsules, lotions and powders in vials or ampoules. Also, the unit dosage form can be a capsule, tablet, cachet, or lozenge itself, or it can be the appropriate number of any of these in packaged form.

It is also possible to administer thalidomide in a time-release formulation. A wide variety of methods are now available in the art for preparing time-release or long-acting compositions. Any of these time-release or long-acting formulations are suitable in the practice of the present invention as long as it does not adversely affect the effectiveness of the thalidomide in the treatment of dermatoses. Advantages of time-release formulations include a lower concentration of peak serum absorption which substantially reduces the adverse side effects and toxicity of the compound administered. In addition, a reduced frequency of administration results, which substantially improves patient compliance. A frequency of administration of every 12 or 24 hours would be preferred. In addition, more constant serum concentration of thalidomide would result thereby allowing a more consistent relief of symptoms.

To prepare dermally applicable formulations it is possible to use the previously mentioned substances and spreadable or liquid hydrocarbons such as Vaseline or paraffin or gels of alkanes and polyethylene, fats and oils of plant or animal origin, which may in part also be hydrated, or synthetic fats such as glycerides of fatty acids $C_8$–$C_{18}$, as well as beeswax, cetyl palmitate, wool wax, wool wax alcohols, fatty alcohols such as cetyl alcohol, stearyl alcohol, polyethylene glycols of molecular weight 200 to 20,000; liquid waxes such as isopropyl myristate, isopropyl stearate, ethyloleate; emulsifiers such as sodium, potassium, ammonium salts of stearic acid or palmitic acid as well as triethalolamine stearate, alkali salts of oleic acid, castor oil acid, salts of sulfurated fatty alcohols such as sodium lauryl sulphate, sodium cetyl sulphate, sodium stearyl sulphate, salts of gallic acid, sterols such as cholesterol, partial fatty acid esters of multivalent alcohols such as ethylene glycol monostearate, glycerol monostearate, pentaerythritol monostearate, partial fatty acid esters of sorbitan, partial fatty acid esters of polyoxyethylene sorbitan, sorbitol ethers of polyoxyethylene, fatty acid esters of polyoxyethylene, fatty alcohol ethers of polyoxyethylene, fatty acid esters of saccharose, fatty acid esters of polyglycerol, lecithin.

Antioxidants that may for example be used are sodium metabisulphite, ascorbic acid, gallic acid, gallic acid alkyl ester, butylhydroxyanisol, nordihydroguaiacic acid, tocopherols as well as tocopherols ±synergitic substances that bind heavy metals through complex formation, for example lecithin, ascorbic acid, phosphoric acid).

Conserving agents that may for example be considered are sorbic acid, p-hydroxybenzoic acid esters (for example lower alkyl esters), benzoic acid, sodium benzoate, trichloroisobutyl alcohol, phenol, cresol, benzethonium chloride and formalin derivatives.

The pharmaceutical and galenic treatment of the active agents is according to conventional standard methods. For example active substances and auxiliary or carrier substances are well mixed by stirring or homogenization (for example using conventional mixing devices), working generally being at temperatures between 20° and 80° C., preferably 20° to 50° C. and, in particular, at room temperature. Reference is made in this context to the following standard work: Sucker, Fuchs, Speiser, Pharmazeutische Technologie, Thieme Verlag Stuttgart, 1978.

EXAMPLE 1

Hard gelatin capsules are prepared using the following ingredients

|  | Quantity (mg/capsules) |
| --- | --- |
| Thalidomide | 250 |
| Starch dried | 200 |
| Magnesium stearate | 10 |

The above ingredients are mixed and filled into hard gelatin capsules in 460 mg quantities.

EXAMPLE 2

A tablet formula is prepared using the ingredients below

|  | Quantity (mg/tablet) |
| --- | --- |
| Thalidomide | 250 |
| Cellulose, microcrystalline | 400 |
| Silicon dioxide, fumed | 10 |
| Stearic acid | 5 |

The components are blended and compressed to form tablets each weighing 665 mg.

EXAMPLE 3

Tablets each containing 60 mg of active ingredients are made up as follows:

| | |
| --- | --- |
| Thalidomide | 60 mg |
| Starch | 45 mg |
| Microcrystalline cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |
| Total | 150 mg |

The active ingredient, starch and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50°–60° C. and passed through a No. 18 mesh U.S. sieve. The sodium carboxymethyl starch, magnesium stearate and talc, previously passed through a No. 60 mesh U.S. sieve, are then added to the granules which, after mixing, are compressed by a tablet machine to yield tablets each weighing 150 mg.

EXAMPLE 4

Capsules each containing 80 mg of medicament are made as follows:

| | |
| --- | --- |
| Thalidomide | 80 mg |
| Starch | 59 mg |
| Microcrystalline cellulose | 59 mg |
| Magnesium stearate | 2 mg |
| Total | 200 mg |

The active ingredient, cellulose, starch and magnesium stearate are blended, passed through a No. 45 mesh U.S. sieve, and filled into hard gelatin capsules in 200 mg quantities.

EXAMPLE 5

Capsules each containing 150 mg of medicament are made as follows:

| | |
|---|---|
| Thalidomide | 150 mg |
| Starch | 164 mg |
| Microcrystalline cellulose | 164 mg |
| Magnesium stearate | 22 mg |
| Total | 500 mg |

The active ingredient, cellulose, starch, and magnesium stearate are blended, passed through a No. 45 mesh U.S. sieve, and filled into hard gelatin capsules in 500 mg quantities.

EXAMPLE 6

A topical ointment containing thalidomide is prepared as follows:

| | % by weight |
|---|---|
| Thalidomide | 20% |
| Vegetable oil | 10% |
| Acetyl lanolin | 10% |
| Lanolin alcohol | 12% |
| Sorbitol sesquioleate | 20% |
| Water add to | 100% |

EXAMPLE 7

A gel is made as follows:

| | % by weight |
|---|---|
| Thalidomide | 15% |
| Carboxyvinyl polymers | 2% |
| Preservative | 0.01% |
| Water add to | 100% |

EXAMPLE 8

An unguent has the following composition:

| | |
|---|---|
| Thalidomide | 6.0 g |
| Stearyl alcohol | 3.0 g |
| Lanolin | 5.0 g |
| Vaseline | 15.0 g |
| d H$_2$O added to | 100.0 g |

EXAMPLE 9

Liposomes containing thalidomide are made as follows: Solutions of lecithin, cholesterol, and an active ingredient in chloroform/ethanol(1:1) or in chloroform/methanol (1:1) are concentrated at about 30 degrees Centigrade in a rotary evaporator, whereby a thin film of lipid and active ingredients forms. Then 8M calcium chloride solution at 60 degrees Centigrade is added to the film, and the liposomes are separated from the wall by manual shaking, The resulting dispersion is then placed in an ultrasonic disintegrator to produce smaller particle sizes and is centrifuged. The combination of liposomes and active ingredient is then washed three times with calcium chloride solution.

Liposomes containing approximately 25–40% by weight are accordingly obtained.

EXAMPLE 10

Ointment containing thalidomide:

| | |
|---|---|
| Thalidomide | 0.9 g |
| Hydrocortisone | 0.1 g |
| Isopropyl myristate | 81.7 g |
| Liquid petrolatum oil | 9.1 g |
| Silica - aerosil 200 | 9.18 g |

CLINICAL APPLICATION OF THE INVENTION

Psoriasis Treatment

General guidance for treatment regimens is obtained from experiments carried out in animal models of the disease of interest. For example, animal models of psoriasis include the analysis of histological alterations in adult mouse tail epidermis (Hofbauer et al., Brit. *J. Dermatol.*, 118:85–99, 1988; Bladon et al., *Arch. Dermatol. Res.*, 277:121–125, 1985, incorporated herein by reference). In this model, antipsoriatic activity is indicated by the induction of a granular layer and orthokeratosis in areas of scale between the hinges of the tail epidermis. Typically, a topical ointment is examined histologically. An additional model is provided by grafting psoriatic human applied daily for seven consecutive days, then the animal is sacrificed, and tail skin is skin to congenitally athymic (nude) mice (Krueger et al., *J., Invest. Dermatol.*, 64:307–312, 1975, incorporated herein by reference). Such grafts have been shown to retain the characteristic histology for up to 11 weeks. As in the mouse tail model, the test composition is applied to the skin at predetermined intervals for a period of one to several weeks, at which time the animals are sacrificed and the skin grafts examined histologically. A third model has been disclosed by Fretland et al. (*Inflammation*, 14:727–739, 1990; incorporated herein by reference). Briefly, inflammation is induced in guinea pig epidermis by topically applying phorbol ester (phorbol-12-myristate-13-acetate; PMA), typically at ca. 2 g/ml in acetone, to one ear and vehicle to the contralateral ear. Test compounds are applied concurrently with the PMA, or may be given orally. Histological analysis is performed at 96 hours after application of PMA. This model duplicates many symptoms of human psoriasis, including edema, inflammatory cell diapedesis and infiltration, high LTB$_4$ levels and epidermal proliferation.

EXAMPLE 11

This example illustrates the treatment of psoriasis.

Twenty patients suffering from psoriasis are to be treated with a cream containing 8% by weight of thalidomide.

In order to establish efficacy of the pharmaceutical composition according to the invention, the clinical test should take the form of a comparison with an appropriate placebo and a commercially available product. This commercially available product should be designated the "control", whereas the cream containing 8% by weight of thalidomide should be the "test" cream.

The clinical trial should be carried out by a consultant dermatologist as a double blind trial, each patient using the test or control creams twice daily, the cream being applied to the area of the arms affected by this skin disorder.

The clinical study should last for a total of four weeks, after which the results should be assessed by the consultant dermatologist. It will be shown that the test cream produces an improvement in the condition of the skin of each patient, as compared with the placebo cream. Furthermore, the "test" cream will be more cosmetically acceptable than the control cream, and will result in fewer complaints from the subjects being treated.

These data will clearly demonstrate that the therapeutic composition according to the invention containing 8% by weight thalidomide is efficacious and, furthermore, is preferred by the patient to a widely used commercially-available pharmaceutical preparation.

EXAMPLE 12

This example illustrates the treatment of acne.

Forty patients suffering from moderate acne are to be treated with a cream containing 5% by weight thalidomide.

In order to demonstrate a significant beneficial effect of the pharmaceutical composition according to the invention, the clinical study should compare this composition with an appropriate placebo (without thalidomide) and another commercially available product specifically prescribed for the treatment of acne.

The clinical study should be performed by a consultant dermatologist and maintained as a double blind trial. Each patient should apply the designated test material twice daily for three months to the affected area.

Upon completion of the treatment period, the areas treated with the 5% by weight thalidomide cream will exhibit a clinically significant decrease in the severity of acne as compared to placebo treatment. Furthermore, the thalidomide-treated subjects will exhibit less severe side effects and complaints as compared to some other commercially available treatments.

EXAMPLE 13

This example illustrates the treatment of Kaposi's sarcoma.

Two patients exhibiting leg lesions and diagnosed as being Kaposi's sarcoma are to be treated with a cream containing 10% by weight thalidomide.

In order to demonstrate the significant beneficial efficacy of the pharmaceutical composition according to the invention, the clinical study should compare this composition with an appropriate placebo (without thalidomide) and another commercially available product specifically prescribed for the treatment of Kaposi's sarcoma.

The clinical study should be performed by a consultant dermatologist and maintained on a double blind trial. Each patient should apply the designated test material twice daily for four weeks to the affected area.

Upon completion of the treatment period, the area treated with the 10% by weight cream will exhibit a clinical improvement and will exhibit less severe side effects.

EXAMPLE 14

Following the protocol of Example 13, two patients are treated except that concurrently with topical administration they are orally treated with 50 mg/day of thalidomide for the duration of the topical treatment.

It is to be understood that the forms of the invention above-described are to be taken as preferred examples of the same, are not to be construed as limiting, and that various changes may be made without departing from spirit of the invention or scope of the appended claims.

What is claimed is:

1. A method for the systemic treatment of inflammatory and autoimmune dermatoses in a mammal which comprises administering to said mammal a therapeutically effective amount of a composition comprising: (a) an effective amount of thalidomide and (b) a therapeutically acceptable vehicle for thalidomide.

2. The method of claim 1 wherein said inflammatory and autoimmune dermatoses are selected from the group consisting of allergic dermatoses, autoimmune skin diseases, vascular dermatoses, seborrheic dermatitis, acne, rosacea, papulosquamous dermatoses, bacterial dermatoses, viral dermatoses, myolic skin infections, granulomatous dermatoses, parasitic skin dermatoses, exfoliative dermatitis, pigmented dermatoses, dermatoses caused by collagen diseases, and dermatoses due to internal diseases.

3. The method of claim 2 wherein one of said dermatoses due to internal disease is Kaposi's sarcoma.

4. The method of claim 2 wherein one of said papulosquamous dermatoses is psoriasis.

5. The method of claim 2 wherein one of said allergic dermatoses is poison ivy.

6. The method of claim 2 wherein said photo-induced dermatitis is sunburn.

7. The method of claim 2 wherein one of said viral dermatoses is chickenpox.

8. The method of claim 2 wherein one of said pigmented dermatoses is vitiligo.

9. The method of claim 1 further including an effective amount of a dermatologic drug selected from the group consisting of menthol, phenol, camphor, coal tar solutions, salicylic acid, aloe vera, vioform, ammoniated mercury, erythromycin, neomycin, garamycin, aureomycin, cortisone, hydrocortisone, resorcinol, sulfur, zinc oxide and mixtures thereof.

10. A method for the systemic treatment of inflammatory and autoimmune dermatoses in a mammal which comprises administering to said mammal a therapeutically effective amount of a composition comprising: (a) an inhibitor selected from the group consisting of cytokine inhibitors, growth factor inhibitors and mixtures thereof and (b) a therapeutically-acceptable vehicle for said inhibitor.

11. The method of claim 10 wherein said growth factor inhibitor is for TNF-alpha.

12. The method of claim 11 wherein said TNF alpha inhibitor is selected from the group consisting of thalidomide and pentoxifylline.

13. A method for the treatment of Kaposi's sarcoma in a mammal which comprises applying to involved areas of the body and/or administering to said mammal a composition comprising: (a) an effective amount of thalidomide and; (b) a therapeutically-acceptable vehicle for the thalidomide.

14. A dermatological composition suitable for treating inflammatory and autoimmune dermatoses in a mammal comprising: a) an effective amount of thalidomide; (b) an effective amount of an addition dermatologic drug selected from one group consisting of menthol, phenol, camphor, coal tar solutions, aloe vera, salicylic acid, vioform, cortisone, hydrocortisone, neomycin, garamycin, sulfur, zinc oxide and mixtures thereof; and (c) a therapeutically acceptable vehicle for the thialidomide.

15. The composition of claim 14 wherein said therapeutically-acceptable vehicle is a mixture of DMSO and propylene glycol.

16. The composition of claim 14 wherein said therapeutically-acceptable vehicle is a liposome.

17. The composition of claim 14 wherein said therapeutically-acceptable vehicle is Vaseline.

18. The composition of claim 14 wherein said therapeutically-acceptable vehicle is lanolin.

19. The composition of claim 14 wherein said therapeutically-acceptable vehicle is propylene glycol.

* * * * *